US007935066B2

(12) United States Patent
Shives et al.

(10) Patent No.: US 7,935,066 B2
(45) Date of Patent: May 3, 2011

(54) INFLATABLE COMPRESSION DRESSING

(75) Inventors: Thomas C. Shives, Rochester, MN (US); Christopher J. Kimble, Pine Island, MN (US); Joel L. Kuhlmann, Rochester, MN (US); Tyler S. King, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 514 days.

(21) Appl. No.: 12/064,271

(22) PCT Filed: Aug. 30, 2006

(86) PCT No.: PCT/US2006/033833
§ 371 (c)(1), (2), (4) Date: Feb. 20, 2008

(87) PCT Pub. No.: WO2007/027755
PCT Pub. Date: Mar. 8, 2007

(65) Prior Publication Data
US 2008/0234616 A1 Sep. 25, 2008

Related U.S. Application Data

(60) Provisional application No. 60/712,461, filed on Aug. 30, 2005.

(51) Int. Cl.
*A61F 5/00* (2006.01)

(52) U.S. Cl. .......................................... 602/13; 602/14
(58) Field of Classification Search ................ 602/5, 13, 602/60–64, 14; 606/201, 204
See application file for complete search history.

(56) References Cited

U.S. PATENT DOCUMENTS 4,803,744 A * 2/1989 Peck et al. ........................ 5/713
5,843,007 A * 12/1998 McEwen et al. ............... 601/152

OTHER PUBLICATIONS

International Search Report corresponding to PCT/US2006/033833 under date of mailing of Jul. 3, 2007.

* cited by examiner

*Primary Examiner* — Kim M Lewis
(74) *Attorney, Agent, or Firm* — Quarles & Brady LLP

(57) ABSTRACT

An improved inflatable compression dressing (10) for use in controlling swelling and promoting healing to wounds subsequent to surgery while allowing visual inspection of the wound during healing is provided. The dressing comprises a bladder (138) formed by an outer wall (114) secured to an inner wall (112) to define an elongated, cup-shaped cavity for receiving an appendage (136); an air supply delivering air to the bladder; and a sensor monitoring air pressure within the bladder and indicating said air pressure to an air pressure control (140). The air pressure control provides air to the bladder at a rate which substantially matches air leaked from the bladder. Thus, the air supply inflates the bladder so as to provide uniform air pressure to the appendage, wherein the appendage is an arm or a leg.

23 Claims, 7 Drawing Sheets

INFLATABLE COMPRESSION DRESSING

CROSS-REFERENCE TO RELATED APPLICATIONS

This application claims priority to U.S. Provisional Appn. No. 60/712,461, filed Aug. 30, 2005, which is hereby incorporated by reference herein.

STATEMENT REGARDING FEDERALLY SPONSORED RESEARCH

Not Applicable.

BACKGROUND OF THE INVENTION

The present invention relates generally to an inflatable compression dressing and, more particularly, to a compression dressing for controlling swelling subsequent to a trauma or surgery by applying a uniform pressure while permitting visual inspection of the wound and adjacent tissue. The dressing of the present invention has wide applicability in the treatment of medical conditions including surgery, fractures, and the like. Additionally, the dressing of the present invention promotes healing by providing active ventilation to the wound and adjacent tissue.

Traditional wound dressings such as the Robert Jones compression dressing protect the wound and apply pressure to promote healing, but are cumbersome to apply and preclude visual inspection of the wound. Further, conventional dressings are not equipped to accommodate residual swelling that occurs to the damaged tissue without binding or rigidly constraining the swelling. Further still, conventional compression dressings are often inadequate when used in conjunction with amputation wound sites, which present additional complications.

Amputations, the removal of the whole or part of an arm/hand or a leg/foot, have become increasingly common. Amputations can be the result of health problems such as diabetes or atherosclerosis, or of trauma, such as from explosions or gunfire. Recovering from amputation surgery is often lengthy due to the variety of complications that can arise. Complications typically consist of problems such as chest infections, angina, strokes, pressure sores, infection and/or necrosis.

Traditional bandage-based compression dressings have long been used to address these complications. However, there are numerous drawbacks to these dressings. First, they are cumbersome as well as difficult and time-consuming to apply. Second, when wrapping a bandage around a wound, it is difficult to wrap the bandage so as to apply a uniform pressure to the wound. Third, they impede airflow around the wound that would promote healing.

Therefore, a need exists for a compression dressing that addresses these and other problems by controlling swelling subsequent to a trauma or surgery by applying a uniform pressure while still permitting visual inspection of the wound and adjacent tissue. Further, it would be desirable to permit airflow around the wound while the dressing is in place.

SUMMARY OF THE INVENTION

The present invention overcomes the aforementioned drawbacks by providing an inflatable compression dressing that controls swelling around the traumatized area by applying a uniform pressure while permitting visual inspection of the wound and adjacent tissue. By "control", we mean the dressing reduces swelling while accommodating whatever residual swelling that may occur without binding or rigidly constraining the swelling. Additionally, the inflatable dressing promotes healing by providing active ventilation to the wound and adjacent tissue.

According to one embodiment, the dressing of the present invention comprises a bladder formed by an outer wall secured to an inner wall to define an elongated, cup-shaped cavity for receiving an appendage when the bladder is filled with air; an air supply delivering air to the bladder; and a sensor monitoring air pressure within the bladder and providing feedback indicating the air pressure within the bladder to an air pressure control. The air pressure control receives the feedback from the sensor and controls the air supply providing air to the bladder. The air supply provides air to the bladder at a rate which substantially matches air leaked from the bladder with air delivered to the bladder. Thus, the air supply inflates the bladder so as to provide uniform air pressure to the appendage, wherein the appendage is an arm, a leg, a hand, a wrist, a foot, an ankle or at least a portion of a head.

The outer and inner walls are formed from a substantially transparent material such as polyvinylchloride or polyurethane, and the inner wall contacts at least a portion of the appendage disposed in the cavity. The inner wall is permeable to air supplied from within the bladder, as well as to water vapor from the appendage. The inner wall is impermeable to liquids.

The dressing also includes a closure device, a ventilation valve and a pressure relief valve. The closure device provides access to the appendage disposed in the cavity. The closure device is selected from the group consisting of straps, hook-and-loop fasteners, adhesives, jacket zippers and sliding zippers.

The ventilation valve allows a controlled amount of air to escape from within the bladder, thereby reducing moisture that may accumulate in the cavity as well as aiding in air exchange/oxygen supply. The ventilation valve may be secured to the outer wall, or it may be secured to the pressure-sensing tube which communicates between the bladder and the air pressure control.

The pressure relief valve is secured to the outer wall and relieves pressure in the bladder in excess of 51 mmHg.

In an alternate embodiment the dressing may accommodate a drainage tube which communicates between the outer atmosphere and the cavity to enable fluids to be removed from the cavity.

In a second embodiment the present invention provides a medical dressing for an appendage comprising a bladder formed by an inner wall shaped in the form of an elongated receptacle having a first opening defining a first cavity and an outer wall shaped in the form of a second elongated receptacle having a second opening defining a second cavity. The second cavity formed by the outer wall surrounds the first cavity formed by the inner wall and the two walls are joined together at a seam positioned at the first and second openings to form a single elongated cavity for receiving an appendage. The appendage can be an arm, a leg, a hand, a wrist, a foot, an ankle or at least a portion of a head.

The dressing includes a closure device operable to provide access to the appendage disposed in the cavity, an air pressure relief valve operable to relieve pressure in the bladder that exceeds 51 mmHg and a ventilation valve secured to a pressure-sensing tube that allows a controlled amount of air to escape from the bladder to remove moisture from within the cavity as well as to aid in air exchange. The dressing may also accommodate a drainage tube which communicates with the cavity to allow fluids to be removed therefrom.

The bladder is inflated around the appendage disposed within the cavity by air received from an air supply. The air pressure within the bladder is monitored by a sensor providing feedback indicating the air pressure within the bladder to an air pressure control. The air pressure control receives the feedback from the sensor and controls the air supply delivered to the bladder so as to provide air to the bladder at a rate which substantially matches air leaked from the bladder. Thus, the air supply inflates the bladder so as to provide uniform air pressure to the appendage disposed within the cavity.

The outer and inner walls of the bladder are formed from a substantially transparent material such as polyvinylchloride or polyurethane, and the inner wall contacts at least a portion of the appendage disposed in the cavity. The inner wall is permeable to air supplied from within the bladder, as well as to water vapor from the appendage. The inner wall is impermeable to liquids.

The outer and inner walls of the bladder comprise flat layers of material, although in an alternate embodiment the inner wall may include pleats of material to provide sufficient material to lay against the appendage disposed within the cavity. Additionally, the inner wall may comprise layers of material on at least one end of the inner wall to prevent the inner wall from bulging out of the dressing.

The outer wall may also include at least one containment flap defined by the outer wall extending around the cavity, thereby preventing the inner wall from bulging out of the dressing.

The closure device, providing access to the appendage disposed in the cavity, is selected from the group consisting of straps, adhesives, jacket zippers, hook-and-loop closures and sliding zippers. In a preferred embodiment the closure device is a jacket zipper. The jacket zipper is secured to the outer wall at a position away from the seam, thereby preventing stress on the seam forming the bladder.

The ventilation valve allows a controlled amount of air to escape from within the bladder, thereby reducing moisture that may accumulate in the cavity as well as aiding in air exchange/oxygen supply. The ventilation valve may be secured to the outer wall, or it may be secured to the pressure-sensing tube which communicates between the bladder and the air pressure control.

In an alternative embodiment, a second sensor may monitor the strain on the inner wall and provide feedback to the air pressure control indicating said strain, the strain being indicative of swelling of the appendage disposed within the cavity.

In an additional alternative embodiment, a third sensor may monitor humidity levels within the cavity and provide feedback indicating the humidity levels within the cavity to the air pressure control. The air pressure control receives the feedback from the sensor and controls the air supply so as to deliver air to the bladder when the humidity within the cavity reaches a certain preset humidity level.

The air pressure of the bladder and the rate at which air is supplied to the bladder is set by the air pressure control. The air pressure and rate of air supply may be set over a wide range, preferably to provide a uniform level of pressure to the bladder. However, in an alternate embodiment, the air pressure control may provide automated, varied pulsation of higher or lower levels of pressure to the appendage.

The dressing of the present invention is particularly useful on wounds created by surgical procedures, especially amputations, fractures and the like. The dressing controls swelling to the wound, helping to prevent bedsores (when the appendage is suspended within the dressing) and promote healing. The dressing facilitates inspection of the wound and surrounding tissue, and provides active ventilation to promote healing and improve patient comfort. Due to its transparent design, the dressing also eliminates the need to periodically remove the dressing to perform inspections of the wound and adjacent tissue, thereby saving time and money as well as reducing patient discomfort. Further, the dressing of the present invention is quick and easy to apply and remove, and remains securely in place once properly applied to a patient, thereby reducing the workload for medical personnel.

In this regard, the dressing can improve patient outcomes while saving both time and money. For instance, it is estimated that the dressing can reduce hospitalization for a major surgery such as an amputation by, for example, at least two days. Additionally, the dressing can reduce or prevent swelling caused by ankle fractures and, thereby, permit earlier surgical repair of a fractured ankle.

Various other features and advantages of the present invention will be made apparent from the following detailed description and the drawings.

DETAILED DESCRIPTION OF THE PREFERRED EMBODIMENT

Figure 1:
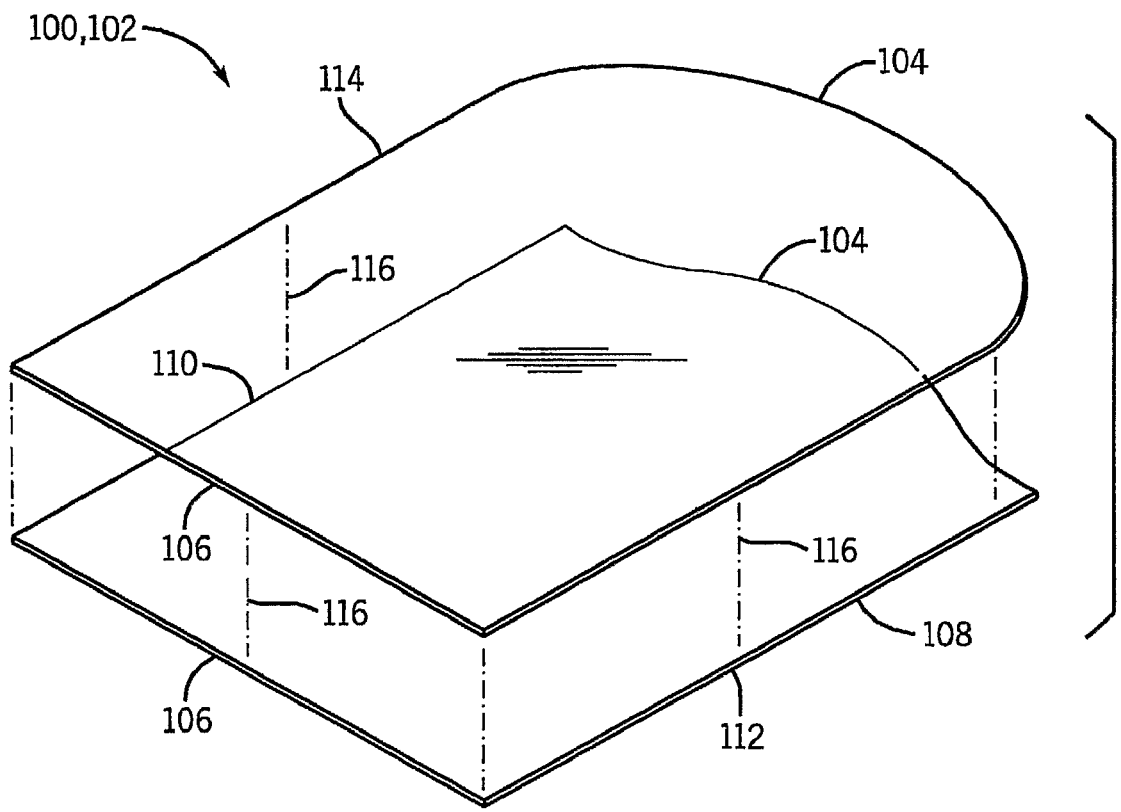
FIG. 1 is an exploded view of one panel of the dressing.
Figure 2:
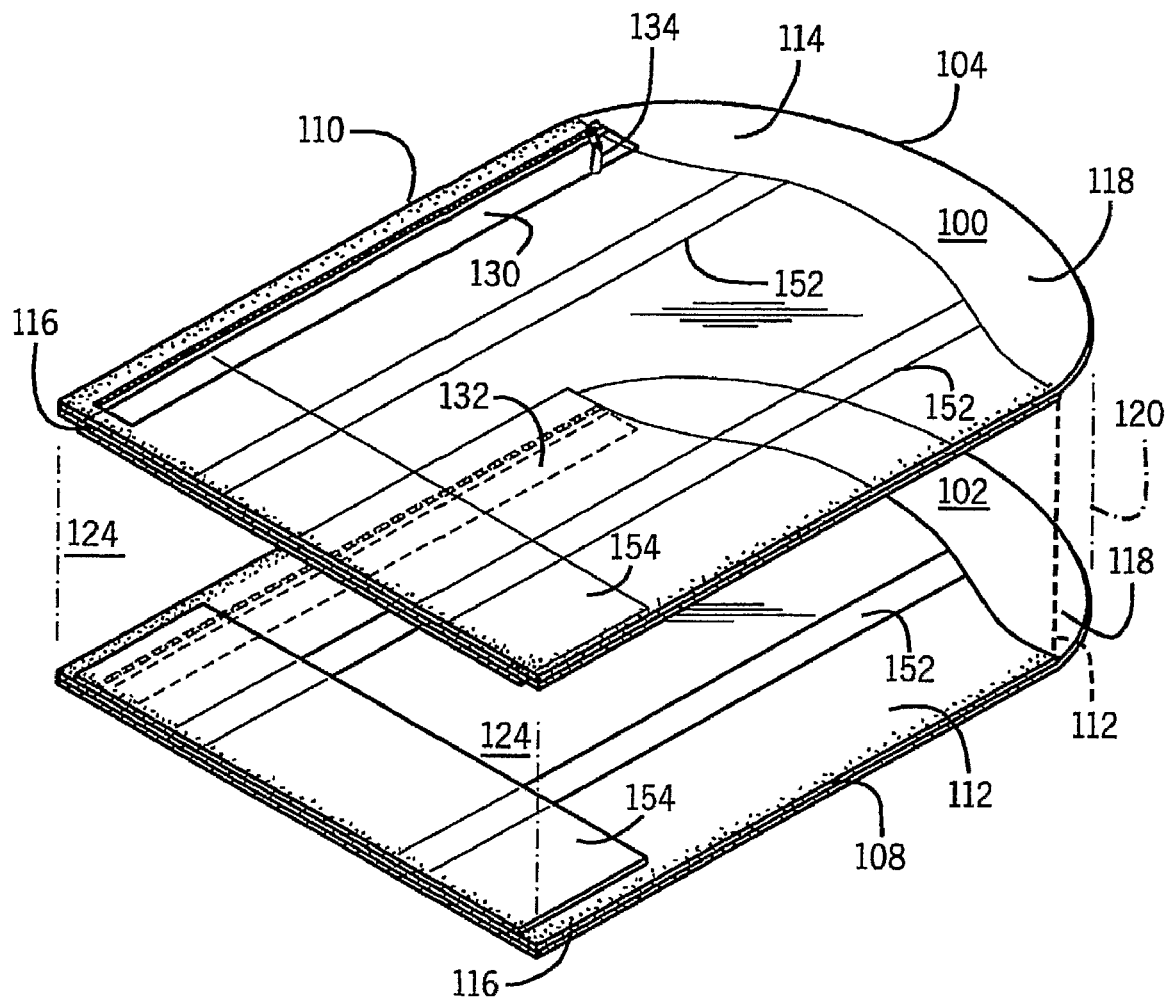
FIG. 2 is an exploded view of both panels of the dressing.
Figure 3:
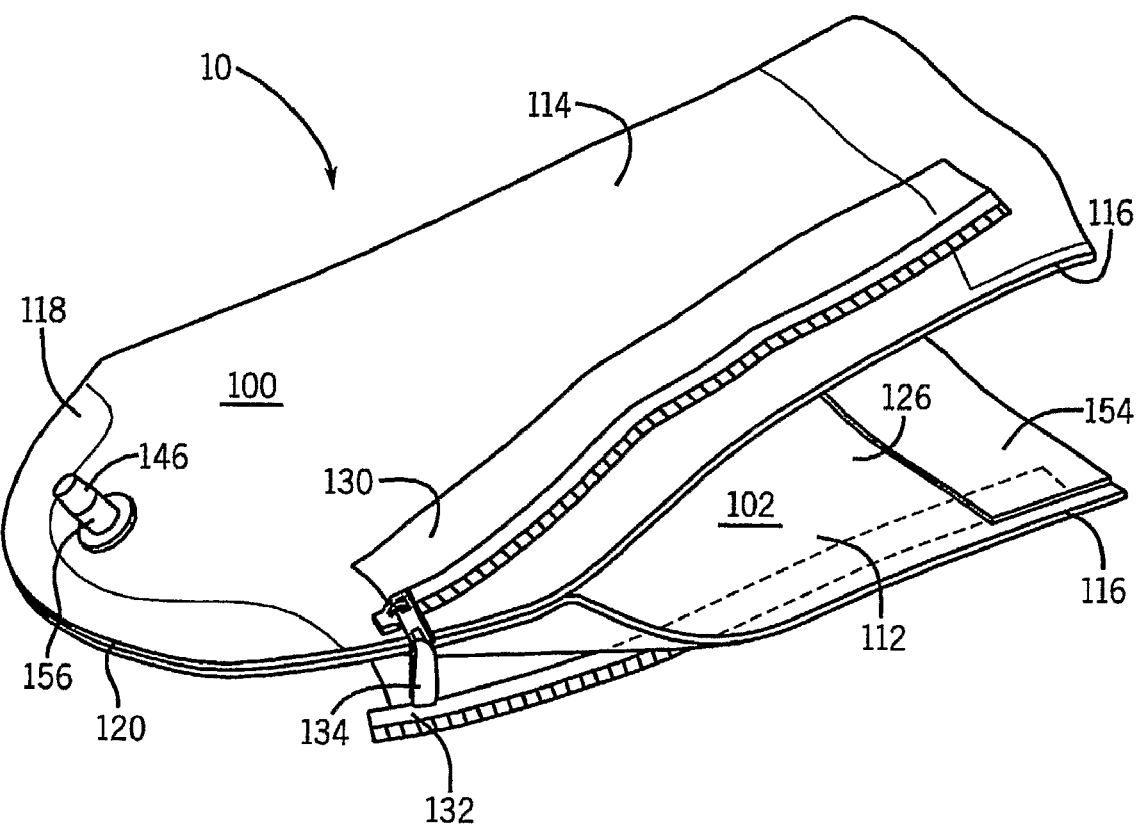
FIG. 3 is a side perspective view of the dressing.
Figure 4:
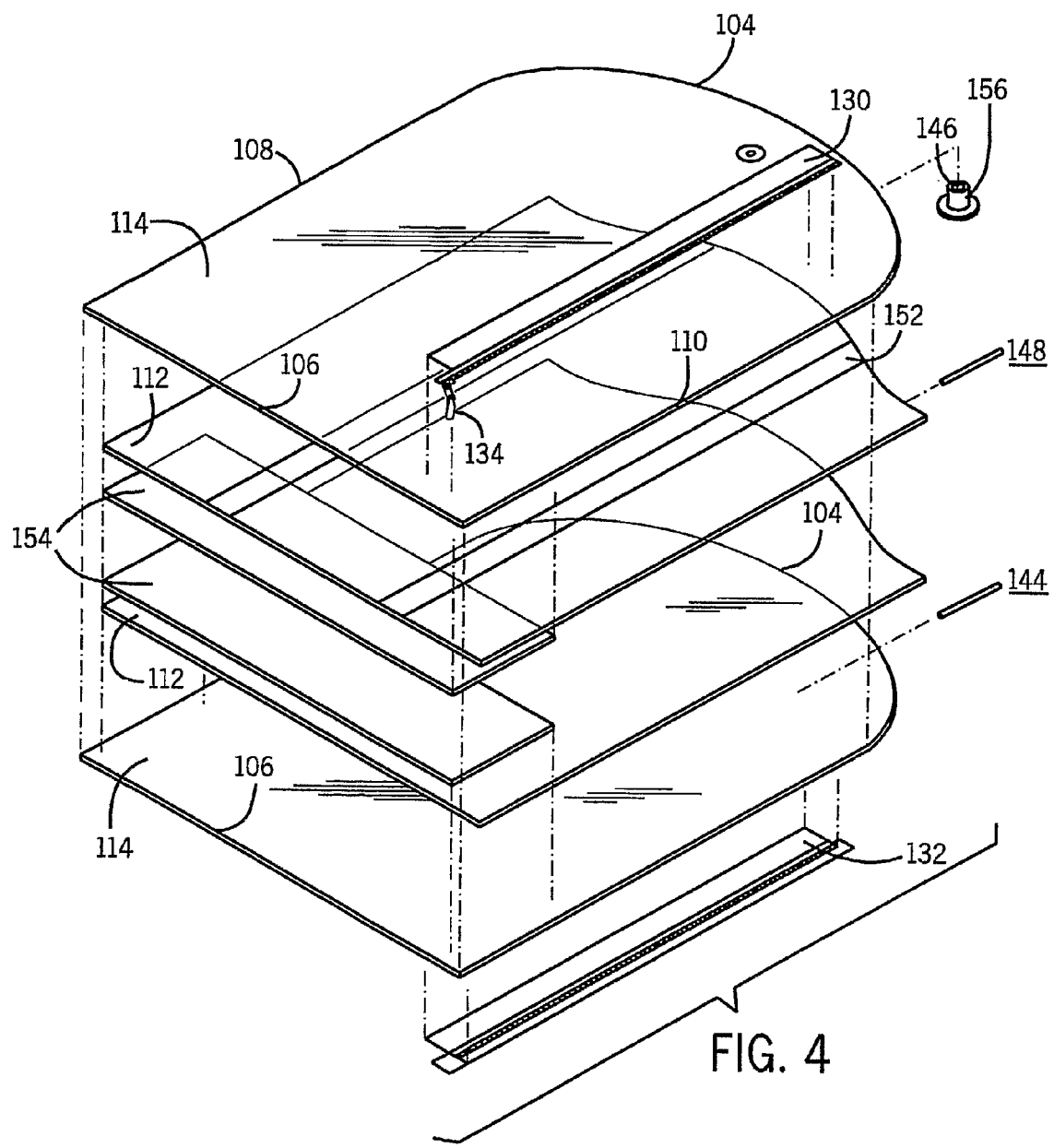
FIG. 4 is an exploded view of the dressing.

The inflatable compression dressing 10 of the present invention provides an improved apparatus for controlling tissue swelling subsequent to surgery for injuries including amputations and the like while allowing visual inspection of the wound while healing.

Referring to FIGS. 1-4, the dressing 10 of the present invention comprises a substantially U-shaped apparatus made up of two substantially U-shaped panels 100 and 102. Each panel 100, 102 has a distal end 104, a proximal end 106 and two opposing sides 108, 110. Each panel also comprises an inner wall 112 and an outer wall 114. For each panel 100, 102, the inner wall 112 is secured to the outer wall 114 in a single airtight seam 116 which runs along the perimeter of the outer wall 114 along the two opposing sides 108, 110 and the proximal end 106. The distal end 104 of the inner wall 112 is not secured to the distal end 104 of the outer wall 114, thereby defining a gap 118 between the inner and outer walls 108, 110.

Figure 7:
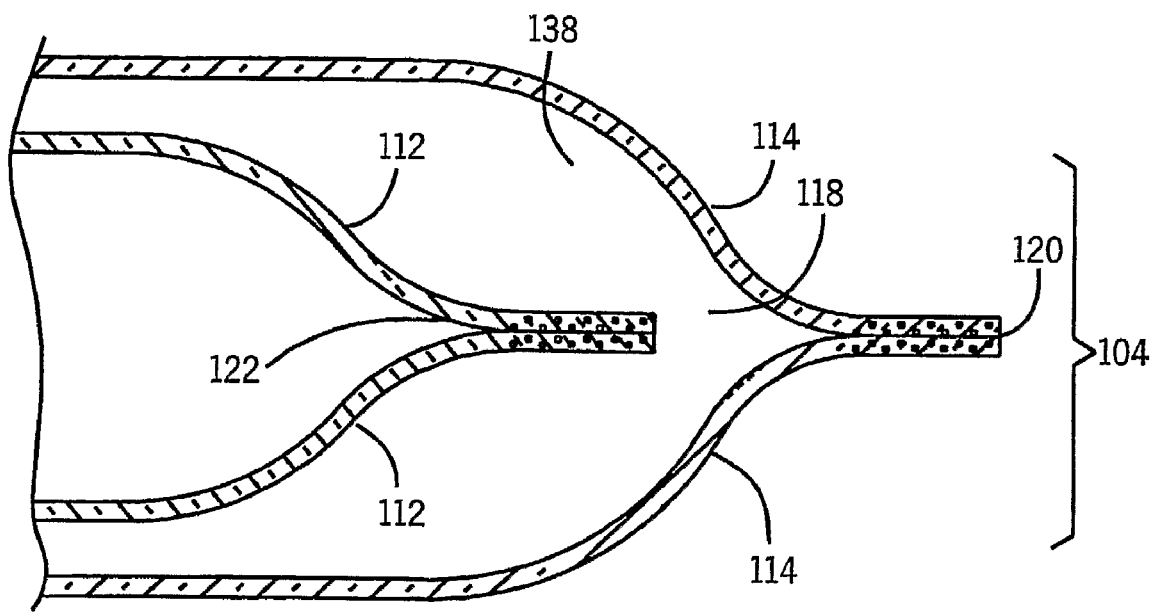
FIG. 7 is a side view of the distal end of the dressing showing the bladder and seams.
Figure 8:
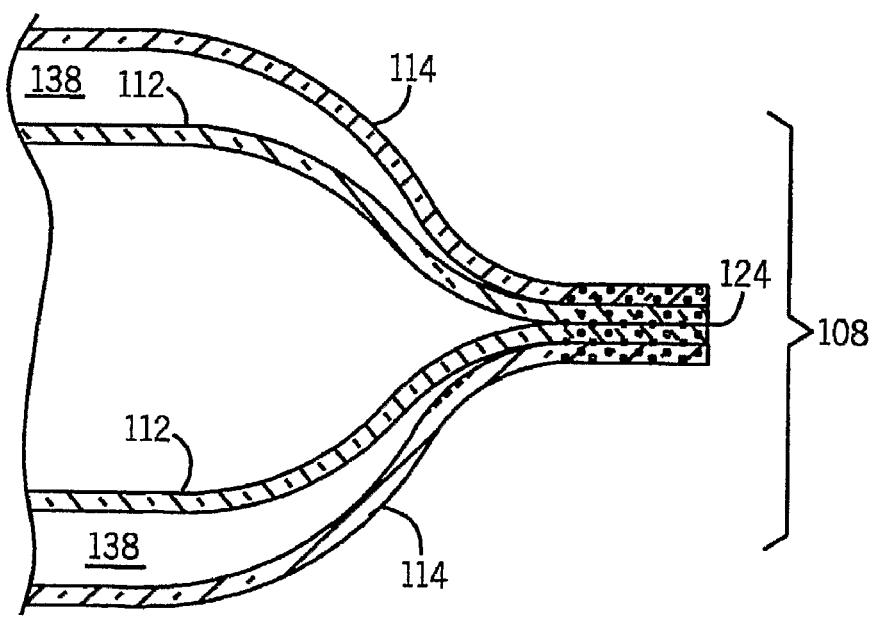
FIG. 8 is a side view of the side of the dressing showing the seam between the two panels of the dressing.

The panels 100, 102 are secured together with the inner walls 112 facing together. The distal ends 104 of the outer walls 114 are joined together to define a first seam 120, and the distal ends 104 of the inner walls 112 are joined together to define a second seam 122 (FIG. 7). The opposing sides 108 of the panels 100, 102 (having the inner and outer walls 112, 114 already joined together at seam 116) are joined together to define a third seam 124 (FIG. 8). Seams 120, 122 and 124 combine to define an airtight bladder 138 between the inner and outer walls 112, 114 of both panels 100, 102.

Joining the two panels 100, 102 at seams 120, 122 and 124 also defines an elongated, substantially cup-shaped cavity 126 that is open on one side 110 and at the proximal end 106. The two open sides 110 are joined together by a closure device 128, shown here as a jacket zipper. The zipper 128 has a first elongated piece 130 secured to the side 110 of the panel 100 and a second elongated piece 132 secured to the side 110 of panel 102. In use, the two pieces 130, 132 are matingly engaged, i.e., zipped together, with a pull tab 134. By closing the two pieces 130, 132 together, the panels 100, 102 are secured together to more clearly define the elongated, substantially cup-shaped cavity 126 configured to receive an appendage 136.

Figure 5:
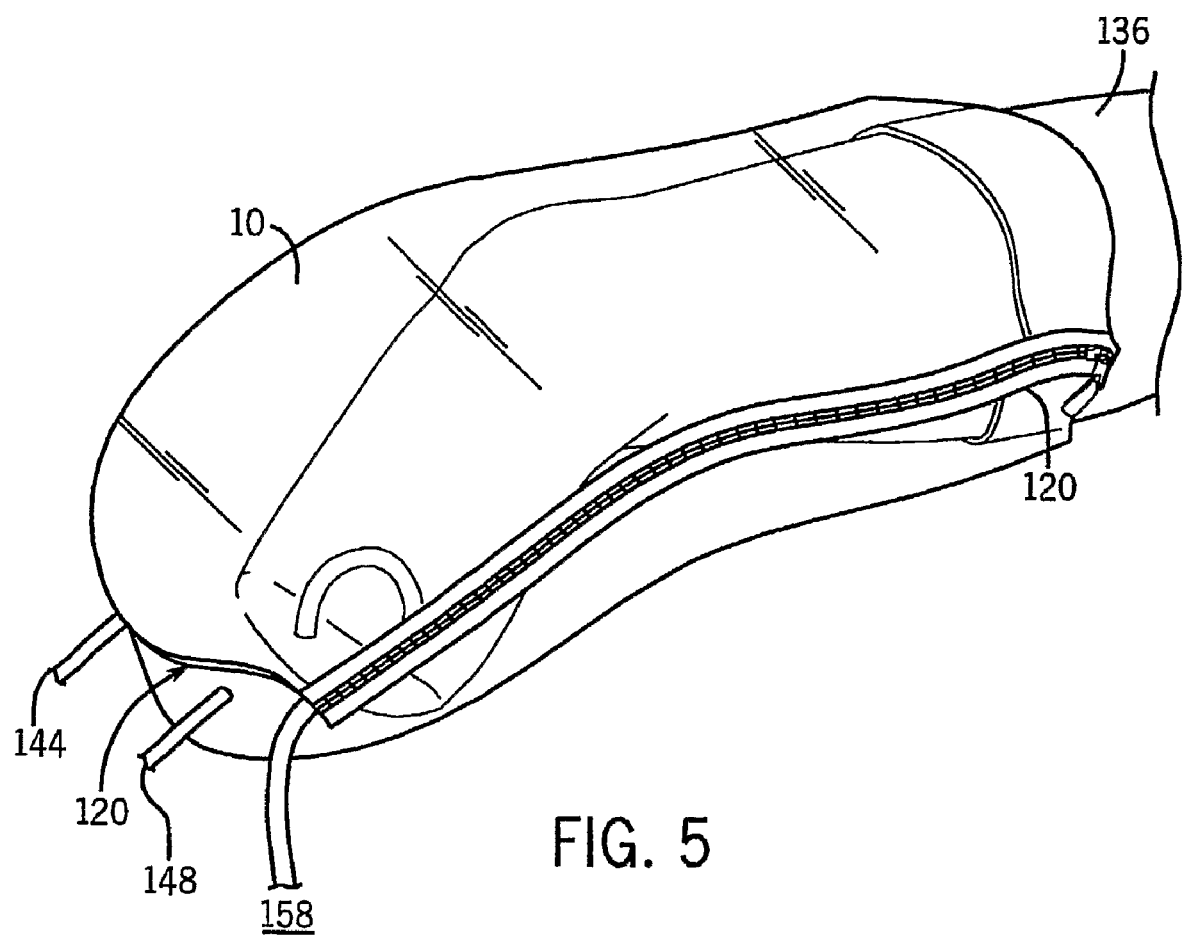
FIG. 5 is a side perspective view of the dressing on an appendage.

As seen in FIG. 5, an appendage 136 is inserted into the proximal end 106 of the dressing 10 and positioned so that the appendage 136 is secured between the inner walls 112 of the panels 100, 102. In use, the bladder 138 is then inflated with air (described in detail below) and secured around the appendage 136 disposed within the cavity 126.

Figure 6:
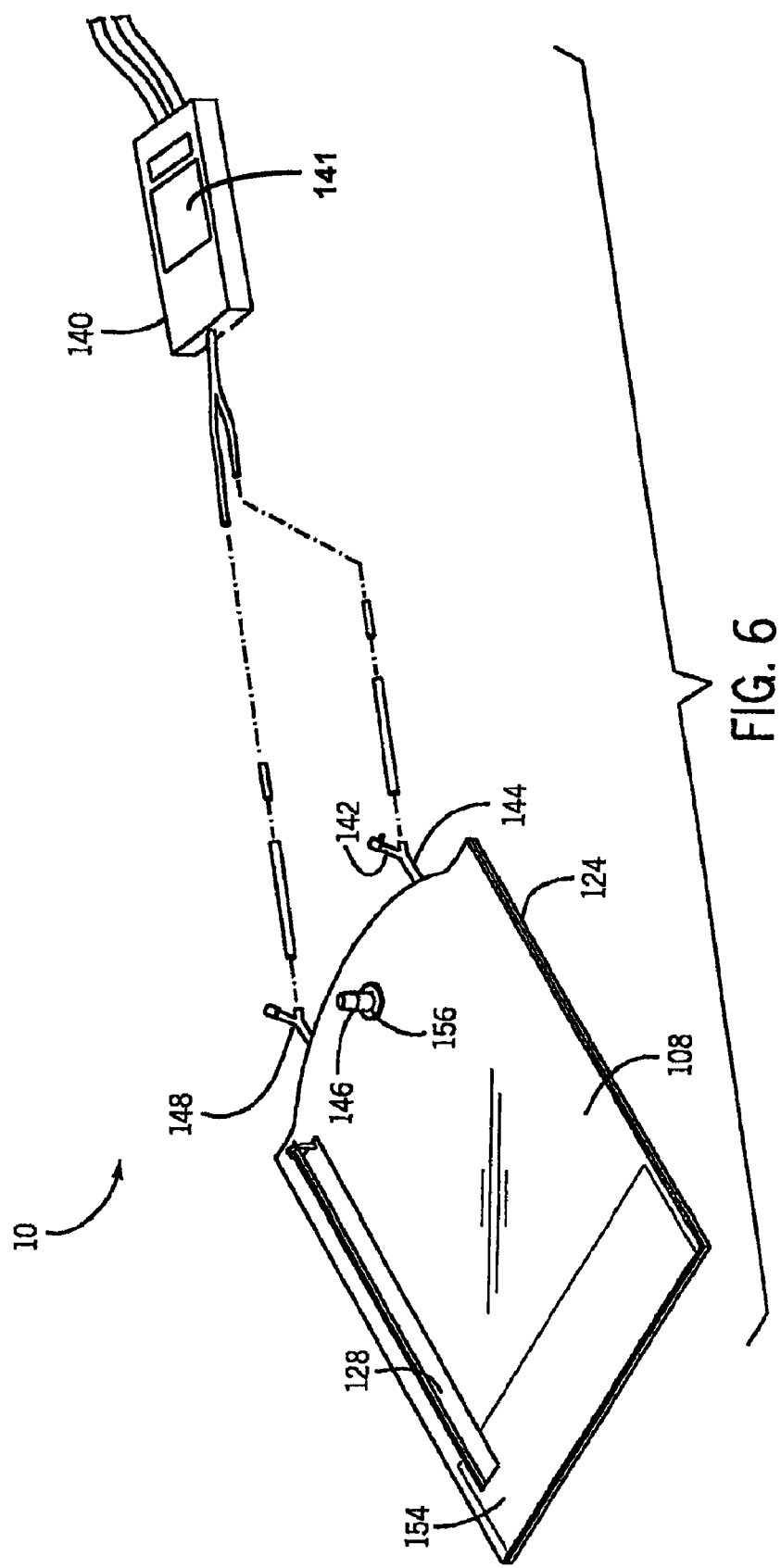
FIG. 6 is a perspective view of the dressing including the air supply, and sensor.

Referring to FIG. 6, the dressing 10 also comprises an air supply delivering air to the bladder 138, a sensor 141 monitoring the air pressure within the bladder 138 and an air pressure control 140 which receives feedback from the sensor and regulates the air supply to provide a uniform air pressure to the bladder 138. The pressure controller 140 includes an electric pump inside it that provides the air supply after the initial inflation with the hand pump. The hand pump is only used to speed up the process of initial inflation.

The dressing 10 also includes at least one closure device 128, a ventilation valve 142, a pressure sense tube 144, a pressure relief valve 146 and an air inlet tube 148.

The overall shape of the dressing 10 may be specifically designed to accommodate a particular anatomical region, appendage, or wound type. The dressing 10 is particularly useful for surgeries to the arm (hand, wrist, elbow, and/or shoulder), leg (hip, knee, ankle), foot (toes, heel) and at least a portion of a patient's head. The dressing 10 may be used on wounds of all types, but is particularly useful for recovering from amputations, fractures and the like.

The inner and outer walls 112, 114 are formed of a suitable inert, biocompatible, flexible, substantially transparent material such as polyvinylchloride or polyurethane. By "substantially transparent" we mean the material allows light colored or clear light to pass through it, and allows one to see through the walls to an appendage disposed within the cavity. The inner wall 112 is formed of a material that is permeable to air and water vapor, yet is impermeable to liquids.

The outer wall 114 is formed of a thick, transparent, polished polyurethane film. The outer wall 114 is preferably about 0.012 inches in thickness. The inner wall 112 is formed of a transparent, breathable polyurethane film suitable for use in direct contact with an open wound. The inner wall 112 is preferably about 0.001 inches in thickness. In a preferred embodiment the inner wall 112 is formed of BioFlex® 130 (Scapa Medical, Windsor, Conn.). While polyurethane film of BioFlex® 130 is preferred, the inner wall 112 may be formed of any substantially transparent, air- and water vapor-permeable material such as Tegaderm® (3M, Minneapolis, Minn.).

In a preferred embodiment the inner and outer walls 112, 114 defining the bladder 138 are untreated. However, in alternative embodiments, the inner wall 112 may be impregnated with antibiotics, antiperspirants, or other pharmaceutical agents. As the inner wall 112, now coated with such agents, is in contact with at least a portion of the appendage 136, the agents are introduced to the appendage 136, thereby expediting the healing process for the underlying wound.

In further alternative embodiments the inner wall 112 may be configured to have a texture or channels to facilitate airflow against the appendage 136. In addition, the permeability of the inner wall 112 may vary according to the type of wound and/or type of appendage 136 the dressing 10 is applied to.

The bladder 138 is defined by the airtight seams 120, 122 and 124. In alternative embodiments additional seams may be added to provide multiple bladders in a single dressing, thereby allowing the dressing to apply different pressures to specific sites of the appendage 136.

The inner and outer walls 112, 114 are preferably comprised of flat layers of material. Flat layers of material provide a smooth, uniform surface without any excess material that visually obscures the appendage. However, the inner walls 112 may also include at least one set of pleats 152 positioned on the distal end 104 of the dressing 10. By providing pleats 152 along the inner walls 112, the inner walls 112 are prevented from pulling away from the appendage 136 due to tangential tension at the point where the inner walls 112 (joined together at seam 122) separate to cover the appendage 136.

The outer walls 114 may also comprise containment flaps 154 around the opening of the cavity 126. The containment flaps 154 help secure the dressing 10 in position around the appendage 136, and also help prevent the inner walls 112 from bulging out of the dressing 10.

Airtight seams 116, 120, 122, 124 are preferably made with radio-frequency welding. Radio-frequency welding, sometimes known as dielectric welding or high frequency (HF) welding, fuses materials together by applying radio frequency energy to the area to be joined. The resulting weld can be as strong as the original materials. However, other methods of securing the seams 116, 120, 122, 124 may also be used, including adhesives, ultrasonic welding, heat sealing and the like. Whichever method is used to secure the walls together, the seams 116, 120, 122, 124 must be able to withstand the pressures to which they are subjected. In the present case, the seams 116, 120, 122, 124 must be able to withstand pressures of at least 90 mmHg. However, in use, the seams 116, 120, 122, 124 will be subjected to a constant air pressure of at least 45 mmHg (a pressure determined to be a safe level with regards to a patient's diastolic pressure).

The closure device 128 is secured to the outer wall 114 of the bladder 138, thereby providing securing the inner and outer walls 112, 114 around the appendage 136 disposed within the cavity 126. The closure device 128 allows a user to access the appendage 136 disposed in the cavity 126 without removing the dressing 10 from the appendage 136. The closure device 128 can be any device known to the art that can withstand a maximum pressure of up to 90 mmHg, including straps, adhesives, hoop-and-loop closures, sliding zippers, jacket zippers, snaps, buttons and button holes, spindles and eyelets and the like. Sliding zippers such as the Slide-Rite® mechanism (wherein two smooth edges are locked together with a sliding tab) were determined to withstand at least 45 mmHg pressure; however, sliding zippers were not compatible with RF welding, requiring the zipper to be stitched in place. Therefore, a nylon jacket zipper, which was determined to be at least six times stronger than the sidling zipper and must also be stitched in place, was chosen as the preferred closure device 128 of the present invention.

The jacket zipper 128 comprises a first elongated piece 130 secured to side 110 of outer wall 114 of panel 100; a second elongated piece 132 secured to side 110 of outer wall 114 of panel 102; wherein the two pieces 130, 132 are matingly engaged together by a pull tab 134. The pull tab 134 locks together the two teethed edges of piece 130, 132. A jacket zipper is preferred because it is the easiest and most comfortable form of closure device 128, requiring little or no effort by the user, and yet provides a strong and secure physical closure to the dressing 10. While other devices known to the art may be used, the closure device 128 employed must be able to attach and detach the panels 100, 102 around the appendage 136 disposed within the cavity 126 at will or on-demand.

The closure device 128 is secured to the outer walls 114 in a position that removes any stress on the airtight seam 116 joining the inner and outer walls 112, 114. Thus, in a preferred embodiment, the closure device 128 is secured to the outer walls 114 at a position away from the seam(s) 116 joining the inner and outer walls 112, 114 of panels 100, 102.

A pressure-sensing tube 144 communicates between the air pressure control 140 and the dressing 10. As seen in FIG. 6, the pressure-sensing tube 144 may include the ventilation valve 142.

The ventilation valve 142 comprises a needle valve extending into the cavity 126 to prevent condensation buildup within the cavity 126. Additionally, the ventilation valve 142 also acts to aid in air exchange between the atmosphere and the cavity 126. The ventilation valve 142 can provide air flow up to the equivalent of a 0.025 inches in diameter opening. However, in a preferred embodiment an opening having a diameter of about 0.010 inches provides the desired one air exchange per hour at nominal pressure. In those instances where the bladder 138 must be airtight, ventilation may be provided in an alternative manner. For example, the bladder 138 may be arranged over an additional layer of transparent material textured with air-filled channels.

The pressure relief valve 146 comprises a generally rigid structure defining at least one central air flow passage. The pressure relief valve 146 is inserted into a flexible plastic flange 156 welded into the outer wall 114 of panel 100. The pressure relief valve 146 releases air from within the bladder 138 to prevent the air pressure from approaching a patient's diastolic blood pressure, defined as the pressure exerted by the blood on the vessel walls when the heart is filling with blood. In short, the pressure relief valve 146 represents a safety feature that prevents the air pressure within the cavity from reaching excessive, potentially hazardous levels.

In use, the pressure relief valve 146 releases air from the bladder 138 when the air pressure approaches and/or exceeds the patient's diastolic pressure. An example of a typical diastolic pressure is 60 mmHg. However, other patients' diastolic pressures may be higher or lower. Therefore, the pressure relief valve 146 of the present invention engages at a pressure no less than 45 mmHg and prevents air pressure within the cavity from exceeding 55 mmHg, preferably preventing the dressing 10 from applying more than 51 mmHg of air pressure to the appendage 136.

In use, when air pressure within the bladder 138 is increased above a predetermined level, i.e., above 51 mmHg, the air pressure within the bladder 138 triggers the valve 146 to move to an open position. Once in the open position, the central air passage is exposed, enabling airflow from the bladder 138 to the atmosphere. In this manner, unsafe levels of air pressure are released from within the bladder 138. Additionally, it is contemplated that a plurality of alternative automated protective systems, preferably mechanical systems, may be included to limit the air pressure to desired levels in the event of a sensor or air pressure control failure.

The dressing 10 of the present invention may also be configured to accommodate a drainage tube 158 comprising a flexible plastic line inserted into the wound after surgery to drain any fluids that may accumulate during healing. In one embodiment, the drainage tube 158 originates in the wound and exits the dressing 10 either through the cavity 126 or the interface between the closure device 128 and the outer wall 114.

The bladder 138 is preferably inflated with air provided by an air supply. In a preferred embodiment two forms of air supply are used. For initial inflation of the bladder 138 around the appendage 136, a manual air supply is used. Once inflated to the proper pressure, an automated air supply (contained within the air pressure control 140) maintains the proper air supply. In some instances, a self-inflating assembly comprising a flexible, helical spring may be used (not shown) to inflate the dressing 10.

Regardless of the type of air supply, air is supplied to the bladder 138 through the air inlet tube 148 communicating between the bladder 138 and the air supply. The air inlet tube 148 passes through the outer wall 114. Any flexible tubing may be used to connect the bladder to the air supply, such as Tygon® tubing.

In a preferred embodiment the air supply provides air to the bladder 138. However, in alternative embodiments, the air supply can provide other substances, such as gaseous medicines or anesthetics, to the bladder 138. In further alternative embodiments, the bladder 138 may be inflated with aerated water. In this embodiment the inner wall 112 must be air permeable, yet impermeable to liquids.

The air supply may be any source of air, such as an air pump which compresses ambient air. However, in alternative embodiments, liquid may be used to provide the pressure within the bladder 138. However, because liquids are relatively incompressible, an external pressure source (not shown) may be required to exert pressure against the appendage 136 disposed within the dressing 10. In this instance, a one-way valve (not shown) is preferably provided to prevent liquid from the bladder from bleeding back out into the air pressure control. The one-way valve may be opened upon command from the air pressure control. When the one-way valve is opened, flow is restricted such that flow only occurs from the air supply to the bladder 138.

The sensor 141 is preferably a pressure transducer which communicates directly with the bladder 138, preferably in the air inlet tube 148 connecting the bladder 138 to the air supply. The sensor continuously monitors the air pressure within the bladder 138 and provides feedback indicating that pressure to the air pressure control 140. The sensor may be a microelectromechanical sensor (MEMS) to monitor the pressure within the bladder 138 and report that pressure to the air pressure control 140. Of course, any sensor known to the art may be used to monitor the pressure within the bladder 138.

In use, as the sensor determines that the rate of air leaking from the bladder 138 to has outpaced the rate of air flow delivered into the bladder 138, the air pressure control 140 responds by increasing the air supply to the bladder 138. The air supply is incrementally increased until the sensor determines that the rate of air leaking from the bladder 138 is substantially the same as the rate of air delivered into the bladder 138.

In an alternative embodiment, the dressing 10 may include one or more strain gauges (not shown) monitoring the strain on the inner wall 112. In this manner, a second sensor (not shown), providing feedback to the air pressure control 140 regarding the strain on the inner wall 112, may also provide feedback to the air pressure control 140 indicating swelling of the appendage 136 disposed within the cavity 126. This is because as the appendage 136 swells, the strain on the inner walls 112 increases, alerting the sensor and air pressure control 140.

Additionally, the dressing 10 may include a third sensor (not shown) to monitor humidity levels within the cavity 126 and provide feedback indicating the humidity levels within the cavity 126 to the air pressure control 140. The air pressure control 140 receives the feedback from the sensor and controls the air supply so as to deliver air to the bladder 138 when the humidity within the cavity 126 reaches a certain preset humidity level. For instance, the humidity levels can be set anywhere from 50% to 80% humidity.

In a preferred embodiment, the air pressure control 140 will adjust the air supply to the bladder to decrease the humidity levels within the cavity when humidity levels in the cavity exceed 65%. For instance, the air pressure control 140 activates the air supply to supply dry air to the bladder 138. As the air pressure in the bladder 138 increases, the moist air in the cavity 126 may escape through the cavity 126 or through the ventilation valve 142.

Alternatively, the air pressure control 140 may also adjust the air supply to the bladder 138 to increase the humidity levels within the cavity 126. However, the humidity levels may only be increased using moisture from the patient (i.e. if the patient is sweating or otherwise leaking fluids). The air-permeable nature of the inner wall 112 of the bladder 138 means that, by increasing and/or decreasing the air supply to the bladder 138, the appendage 136 disposed within the cavity 126 will also be exposed to and ventilated by an increased and/or decreased amount of air. Humidity levels within the cavity 126 may also be controlled via separate humidity-control assembly secured around the exterior of the dressing (not shown).

The sensor reports directly to the air pressure control 140. The air pressure control 140 responds to feedback received from the sensor indicating the air pressure within the bladder 138, and controls the air supply so as to maintain a uniform air pressure within the bladder 138. Due to the air- and water vapor-permeable inner wall 112, air escapes from the bladder 138 at a steady rate (thereby ventilating the appendage 136 disposed within the cavity 126). Thus, the air pressure control 140 determines the rate of air that must be reintroduced to the bladder 138 to substantially equal the rate of air escaping from the bladder 138. Therefore, though air is allowed to "leak" from the bladder 138 into the cavity 126 to ventilate the wound, a constant, uniform pressure is maintained within the bladder 138, and therefore, is applied to the appendage 136.

The air pressure within the bladder 138, controlled via the sensor and air pressure control 140, can be varied over a wide, user-selectable range. For instance, the air pressure within the bladder 138 can range anywhere from 12 mmHg to 45 mmHg, depending on the nature of the wound and the trauma to the appendage 136.

The air pressure control 140 determines the air pressure within the bladder 138, and preferably provides a uniform amount of pressure to the bladder 138. However, in an alternative embodiment, the air pressure control 140 may be adjusted so as to provide regular pulses of higher and/or lower pressure to the bladder 138, and thus to the appendage 136 disposed within the dressing 10. The pulsating pressure can be in periodic bursts of pressure, but more preferably includes slow undulations of applied pressure. Increased pressure to the appendage 136 can stimulate blood flow and promote healing. Automated pulsation of pressure may also be provided via separate automated pulsation assembly secured around the exterior of the dressing (not shown).

In use, a wounded appendage 136 is inserted into the cavity of a non-inflated dressing 10. The dressing 10 is positioned as desired around the appendage 136 and the closure device 128 is closed, securing the panels 100, 102 together at side 110. The bladder 138 is then inflated, preferably with a manual hand pump or other air supply, to a certain predetermined pressure level. The bladder 138 is then connected to the sensor and air pressure control 140 (containing the automated air supply). In this manner, the dressing 10 provides uniform pressure to the appendage 136 disposed within the dressing 10.

As the appendage 136 heals, the air pressure control 140 and sensor act in combination to maintain a uniform air pressure within the bladder 138. The air pressure control 140 responds to changes in air pressure within the bladder 138. For instance, when the appendage 136 disposed within the cavity 126 swells during healing (as is expected), the air pressure within the bladder 138 tends to increase above the regulated pressure setting. In response, air passes through the air-permeable inner wall 112 into the cavity 126 and/or out through the ventilation valve 142, thereby restoring the pressure within the bladder 138 to the proper levels and ventilating the appendage 136 in the process.

In a preferred embodiment the air pressure provided to the bladder 138 helps to secure the dressing 10 in position around the appendage 136, partially due to frictional forces between the inner wall 112 and the appendage 136 itself. However, in alternative embodiments, the dressing 10 may be secured around the appendage 136 with such things as a hook-and-loop closure and the like (not shown).

The dressing 10 provides up to at least 45 mmHg pressure to the appendage. However, if additional pressure is desired, nylon straps or a clear, rigid shell (not shown) may surround the dressing to increase pressure against the underlying appendage 136.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A medical dressing for an appendage comprising:
   a bladder formed by an inner wall shaped in the form of an elongated receptacle having a first opening defining a first cavity and an outer wall shaped in the form of a second elongated receptacle having a second opening defining a second cavity, wherein the second cavity formed by the outer wall surrounds the first cavity formed by the inner wall, and a seam joins the inner and outer walls together at the first and second openings such that the inner wall forms a single elongated cavity for receiving an appendage;
   a closure device secured to the outer wall and being operable to close the bladder around the appendage disposed in the cavity;
   an air pressure relief valve secured to the outer wall and being operable to relieve pressure in the bladder in excess of 51 mmHg;
   a ventilation valve secured to the outer wall and being operable to enable a controlled amount of air to escape from the bladder and thereby reduce moisture within the cavity;
   an air supply delivering air to the bladder thereby inflating the bladder around the appendage disposed in the cavity;
   a sensor monitoring air pressure within the bladder and providing feedback indicating the air pressure within the bladder;
   an air pressure control receiving the feedback from the sensor and controlling the air supply to substantially match a rate of air delivered to the bladder with a rate of air leaked from the bladder into the cavity;
   wherein the dressing provides uniform air pressure to the appendage.

2. The medical dressing of claim 1 wherein the appendage is selected from the group consisting of an arm, a leg, a hand, wrist, foot, ankle or at least a portion of a head.

3. The medical dressing of claim 1 wherein the inner wall contacts at least a portion of the appendage disposed in the pocket, the inner wall being permeable to air flow therefrom.

4. The medical dressing of claim 1 wherein the inner wall contacts at least a portion of the appendage disposed in the pocket, the inner wall being permeable to water vapor therefrom.

5. The medical dressing of claim 1 wherein the inner wall is impermeable to liquid.

6. The medical dressing of claim 1 wherein the outer wall and the inner wall are formed from a substantially transparent material.

7. The medical dressing of claim 6 wherein the outer wall and inner wall are formed from polyurethane or polyvinylchloride.

8. The medical dressing of claim 1 wherein the outer wall and inner wall comprise flat layers of material.

9. The medical dressing of claim 1 wherein the inner wall includes pleats to prevent the inner wall from pulling away from the appendage.

10. The medical dressing of claim 1 further comprising at least one containment flap defined by the outer wall extending around the opening of the cavity, wherein the containment flap prevents the inner wall from bulging out of the dressing.

11. The medical dressing of claim 1 wherein the inner wall comprises multiple layers of material on at least one end to prevent the inner wall from bulging out of the dressing.

12. The medical dressing of claim 1 wherein the closure device is selected from the group consisting of straps, hook-and-loop fasteners, adhesives, jacket zippers and sliding zippers.

13. The medical dressing of claim 12 wherein the closure device is a jacket zipper having a first elongated piece matingly engaged with a second elongated piece by a pull tab.

14. The medical dressing of claim 13 wherein the first elongated piece is secured to one end of the outer wall and the second elongated piece is secured to an opposing end of the outer wall, wherein when the first and second elongated pieces are matingly engaged together by the pull tab, the closure device secures the outer walls together.

15. The medical dressing of claim 1 wherein the closure device is secured to the outer wall at a position away from the seam, thereby preventing stress on the seam.

16. The medical dressing of claim 1 further comprising a pressure-sensing tube which communicates between the bladder and the air pressure control.

17. The medical dressing of claim 1 further comprising a self-inflating assembly secured to the outer wall.

18. The medical dressing of claim 1 wherein a second sensor monitors strain on the inner wall of the dressing and provides feedback of that strain to the air pressure control to quantify swelling of the appendage.

19. The medical dressing of claim 1 wherein the air pressure and rate is set by the air pressure control.

20. The medical dressing of claim 19 wherein the air pressure and rate may be set so as to apply automated pulsation of applied pressure to the appendage.

21. The medical dressing of claim 1 wherein a third sensor monitors humidity levels within the cavity and provides feedback indicating the humidity levels within the cavity to the air pressure control and the air pressure control receives the feedback from the sensor and controls the air supply to adjust the humidity within the cavity when the cavity reaches a certain preset humidity level.

22. The medical dressing of claim 21 wherein the air pressure control adjusts the humidity within the cavity by pumping moist air or dry air into the cavity.

23. The medical dressing of claim 1 wherein the outer wall may accommodate a drainage tube communicating with the cavity to enable fluids to be removed therefrom.

* * * * *